(12) United States Patent
Guo et al.

(10) Patent No.: US 8,958,063 B2
(45) Date of Patent: Feb. 17, 2015

(54) ILLUMINATION SYSTEM FOR DETECTING THE DEFECT IN A TRANSPARENT SUBSTRATE AND A DETECTION SYSTEM INCLUDING THE SAME

(75) Inventors: Xiaofeng Guo, Shanghai (CN); Huifen Li, Shanghai (CN); Xiaofeng Lin, Shanghai (CN); Xiaowei Sun, Shanghai (CN); Wenhua Deng, Shanghai (CN)

(73) Assignee: Saint-Gobain Glass France, Courbevoie (FR)

( * ) Notice: Subject to any disclaimer, the term of this patent is extended or adjusted under 35 U.S.C. 154(b) by 0 days.

(21) Appl. No.: 14/369,384

(22) PCT Filed: Dec. 31, 2011

(86) PCT No.: PCT/CN2011/085131
§ 371 (c)(1),
(2), (4) Date: Jun. 27, 2014

(87) PCT Pub. No.: WO2013/097215
PCT Pub. Date: Jul. 4, 2013

(65) Prior Publication Data
US 2014/0347657 A1    Nov. 27, 2014

(51) Int. Cl.
*G01N 21/00*  (2006.01)
*G01N 21/88*  (2006.01)
*G01N 21/958* (2006.01)
*F21K 99/00*  (2010.01)
*F21Y 103/00* (2006.01)

(52) U.S. Cl.
CPC .......... *G01N 21/8806* (2013.01); *G01N 21/958* (2013.01); *F21K 9/175* (2013.01); *G01N 2021/8816* (2013.01); *G01N 2201/105* (2013.01); *F21Y 2103/003* (2013.01)
USPC ................... 356/239.1; 356/237.3; 356/239.6

(58) Field of Classification Search
CPC ..... G01N 33/544; G01N 33/66; A61B 5/0066
USPC ................... 356/237.1–237.6, 239.1–239.8
See application file for complete search history.

(56) References Cited

U.S. PATENT DOCUMENTS 7,453,563 B2    11/2008 Rudert et al.
2008/0304055 A1*  12/2008 Oshima et al. ............. 356/237.5

FOREIGN PATENT DOCUMENTS

| CN | 201527404 | 7/2010 |
| CN | 101900689 | 12/2010 |
| JP | H11-337504 | 12/1999 |

OTHER PUBLICATIONS

International Search Report issued for International Application No. PCT/CN2011/085131, dated Oct. 18, 2012.

*Primary Examiner* — Kara E Geisel
*Assistant Examiner* — Iyabo S Alli
(74) *Attorney, Agent, or Firm* — Pillsbury Winthrop Shaw Pittman LLP (57) ABSTRACT

An illumination device for providing near isotropic illumination, and particularly an illumination system for detecting the defect in a transparent substrate and a detection system including the same are presented. An illumination system includes: an illumination system for detecting the defect in a transparent substrate, including light source receptacle in bar shape; first spot light sources, each emitting a respective first light, the respective first lights being substantially parallel to each other and the first spot light sources being arranged to a first line of spot light sources along the longitudinal direction of the receptacle; and second spot light sources, each emitting a respective second light, the respective second lights being substantially parallel to each other and the second spot light sources being arranged to a second line of spot light sources along the longitudinal direction of the receptacle.

26 Claims, 5 Drawing Sheets

ILLUMINATION SYSTEM FOR DETECTING THE DEFECT IN A TRANSPARENT SUBSTRATE AND A DETECTION SYSTEM INCLUDING THE SAME

CROSS-REFERENCE TO RELATED APPLICATIONS

This application is the U.S. National Stage of PCT/CN2011/085131, filed Dec. 31, 2011. The content of this application is incorporated herein by reference in its entirety.

FIELD OF THE INVENTION

The invention relates to illumination device for providing near isotropic illumination, and particularly to an illumination system for detecting the defect in a transparent substrate and a detection system including the same.

BACKGROUND OF THE INVENTION

The present invention relates to an illumination system designed to improve the detectability of some directional defects, such as bubble, in AOI system for detecting the defect in a transparent substrate, for example, a glass substrate.

In line scan AOI system, linear LED bar is normally used as illuminations. With the illumination of these linear LED bar, most defects could be detected by CCD camera. However, some directional defects, such as bubble, present great difference in signal intensity when the direction of defect is different. When a bubble is illuminated by linear LED bar and detected by AOI system, the detectability of bubble with its major axis setting along CCD scan line is very high while the detectability of bubble with its minor axis setting along CCD scan line could be quite low.

Figure 1A:
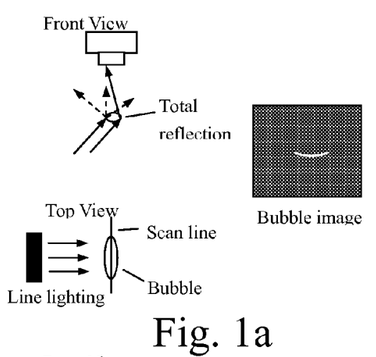
FIG. 1 is an illustration of lighting and bubble images with linear lighting and line scan CCD camera based on the prior art.
Figure 1B:
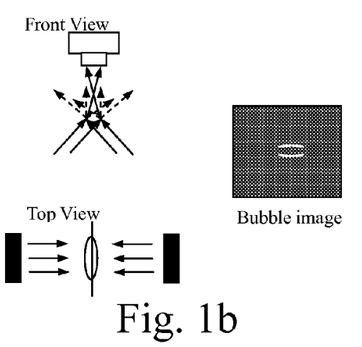

As shown in FIG. 1a, when bubble is set along with scan line with only one linear lighting set at one side of scan line, only part of bubble will be illuminated with strong enough intensity. The reason might be: (a) in one edge of bubble, lighting enters bubble and total reflection happened at air-glass interface so that most of the energy of lighting is reflected into CCD camera; (b) in another edge of bubble, lighting is mainly reflected by glass-air interface and limited energy is transmitted and finally received by CCD. While setting two lighting at both sides of scan line respectively, as shown in FIG. 1b, more part of bubble could be illuminated with strong enough intensity. In this case, most part of bubble is illuminated with strong enough intensity and bubble could be easily detected and classified.

Figure 1C:
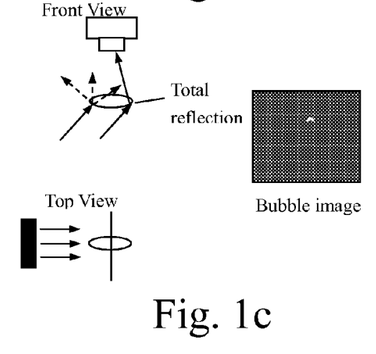
Figure 1D:
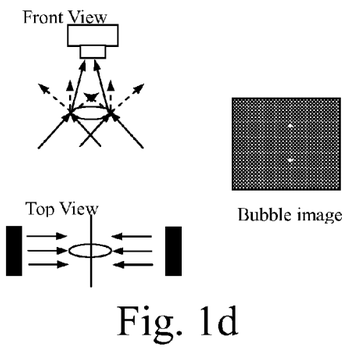

If bubble is set perpendicular to scan line with one linear lighting, however, as shown in FIG. 1c, much less part of bubble could be illuminated with strong enough intensity. Even if two linear lightings are set at both sides of scan line, as shown in FIG. 1d, the light from bubble is still not strong enough for good detection and classification.

Figure 2A:
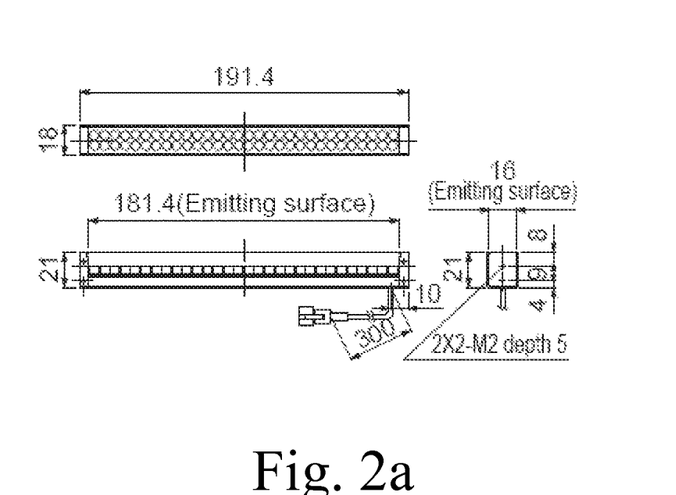
FIG. 2*a* shows a linear LED lighting bar for line scan CCD camera in the prior art.
Figure 2B:
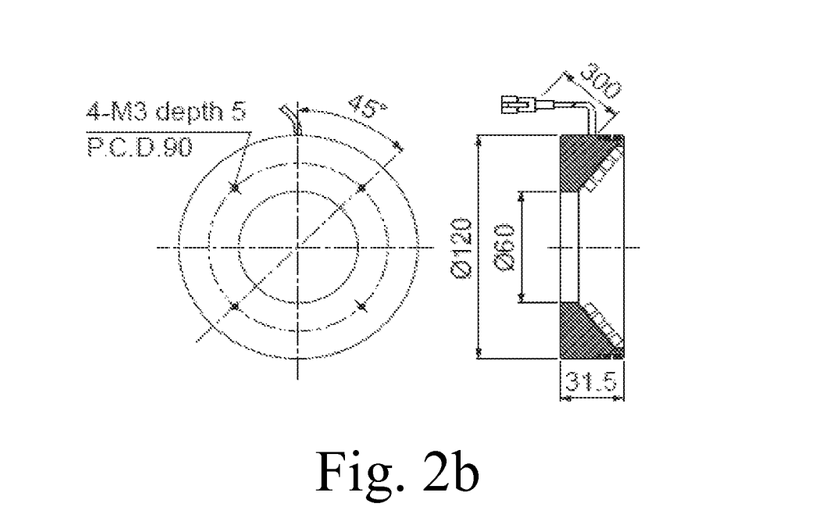
FIG. 2*b* shows a ring LED lighting for area CCD camera.

In area scan AOI system, area lighting such as round LED or rectangle LED is set as illumination. The detectability of bubble does not depend on the direction of bubble in such kind of system. The difference between area lighting and line lighting is obvious. By line illumination, bubble is illuminated by lighting from almost one direction, as shown in FIG. 2a. While by area illumination, bubble is illuminated by lighting from all directions, as shown in FIG. 2b. This difference could show the reason that detectability of bubble depends on its direction in line scan system.

However, it's difficult to adapt area lighting to line scan system due to the big dimension of some line scan system for the large-dimension transparent substrate. It's almost impossible to have area lighting with length in several meters.

Therefore, a novel illumination system for providing near isotropic illumination is designed to solve mentioned problem in this invention disclosure.

SUMMARY OF THE INVENTION

The present invention is on the basis of the insight that, to realize a near isotropic illumination system with low cost, every point on the scan line of the detection system should have lighting from both directions along the scan line, i.e., every point on the scan line should be illuminated from both directions along the scan line. Furthermore, every point on the scan line should have lighting from both directions perpendicular to the scan line as well so that the defects, mostly bubble, with minor axis along the scan line could be well illuminated.

To achieve the above purpose, the illumination light source used for the detection system should provide at least four sets of lights, which can provide the above-mentioned lighting from the four directions, i.e., the four sets of lights have components of lights in both directions along the scan line and in both directions perpendicular to the scan line.

In practice, the components of lights in both directions perpendicular to the scan line could be implemented by adopting two illumination systems disposed at both sides of the scan line of the line scan AOI system. Furthermore, each illumination systems may have two sets of light sources providing two sets of lights, each set of lights being substantially parallel to each other and providing lighting in one of both directions along the scan line. Thus, the effect of bubble direction on detectability of the line scan AOI system could be erased.

In accordance with the present invention, the two sets of light sources in each illumination system may be arranged to be parallel with each other, or may be alternately arranged in a line, or in other forms, as along as each point on the scan line has lighting from both directions along the scan line.

According to one aspect of the present invention, it provides an illumination system for detecting the defect in a transparent substrate, including:

light source receptacle in bar shape;

a plurality of first spot light sources, each emitting a respective first light, the respective first lights being substantially parallel to each other and the first spot light sources being arranged to a first line of spot light sources along the longitudinal direction of the receptacle; and a plurality of second spot light sources, each emitting a respective second light, the respective second lights being substantially parallel to each other and the second spot light sources being arranged to a second line of spot light sources along the longitudinal direction of the receptacle, wherein the first line of spot light sources and the second line of spot light sources are substantially arranged in a line, the first line of spot light sources and the second line of spot light sources locate in different half of the receptacle in the longitudinal direction, the first light and the second light converge to a scan line, and the projections of the first and the second lights, which are converged at each point on the scan line, in a plane P passing the scan line and perpendicular to the transparent substrate are located at different sides of a line in the plane P, which passes the point and is perpendicular to the scan line.

In an embodiment, the angle between the projection of the first light in the plane P and the line 1 is from 37.5° to 52.5°, and the angle between the projection of the second light in the plane P and the line 1 is from 37.5° to 52.5°.

In an embodiment, the first spot light sources are substantially arranged on the receptacle along a straight line and the second spot light sources are substantially arranged on the receptacle along the straight line.

In another embodiment, the first spot light sources are substantially arranged on the receptacle along a curve and the second spot light sources are substantially arranged on the receptacle along the curve.

According to another aspect of the present invention, it provides an illumination system for detecting the defect in a transparent substrate, including:

light source receptacle in bar shape;

a plurality of first spot light sources, each emitting a respective first light, the respective first lights being substantially parallel to each other and the first spot light sources being arranged to a first line of spot light sources along the longitudinal direction of the receptacle; and a plurality of second spot light sources, each emitting a respective second light, the respective second lights being substantially parallel to each other and the second spot light sources being arranged to a second line of spot light sources along the longitudinal direction of the receptacle, wherein the first line of spot light sources and the second line of spot light sources are substantially arranged in parallel, the first light and the second light converge to a scan line, and the projections of the first and the second lights, which are converged at each point on the scan line, in a plane P passing the scan line and perpendicular to the transparent substrate are located at different sides of a line in the plane P, which passes the point and is perpendicular to the scan line.

In an embodiment, the angle between the projection of the first light in the plane P and the line 1 is from 37.5° to 52.5°, and the angle between the projection of the second light in the plane P and the line 1 is from 37.5° to 52.5°.

In an embodiment, the first spot light sources are substantially arranged on the receptacle along a straight line and the second spot light sources are substantially arranged on the receptacle along a straight line. In other words, the two straight lines are parallel to each other.

In another embodiment, the first spot light sources are substantially arranged on the receptacle along a curve and the second spot light sources are substantially arranged on the receptacle along a curve.

According to another aspect of the present invention, it provides an illumination system for detecting the defect in a transparent substrate, including:

light source receptacle in bar shape;

a first set of spot light sources, including a plurality of first light sources a, the first light sources a being substantially arranged in a line to a first line of spot light sources (1a, 2a, . . . ka, . . . na) along the longitudinal direction of the receptacle, wherein n is an integer larger than 2, k is an integer between 1 and n, and each first light source a emits a first light; and a second set of spot light sources, including a plurality of second light sources b, the second light sources b being substantially arranged in a line to a second line of spot light sources (1b, 2b, . . . kb, . . . nb) along the longitudinal direction of the receptacle, wherein each second light source b emits a second light, wherein the first light emitted by the first light source 1a and the second light emitted by the corresponding second light source 1b converge to a first scan dot 1s, . . . , the first light emitted by the first light source ka and the second light emitted by the corresponding second light source kb converge to a kth scan dot ks, . . . , the first light emitted by the first light source na and the second light emitted by the corresponding second light source nb converge to an nth scan dot ns, and the first scan dot 1s, . . . , the kth scan dot ks, . . . , and the nth scan dot ns are substantially arranged in a continuous straight line or curve, wherein the projections of the first and the second lights, which are converged at each point on the scan line, in a plane P passing the scan line and perpendicular to the transparent substrate are located at different sides of a line in the plane P, which passes the point and is perpendicular to the scan line.

In an embodiment, the lines in which the first set of spot light sources and the second set of spot light sources are arranged are substantially parallel to each other.

In another embodiment, the line in which the first set of spot light sources are arranged is in the extended line of the line in which the second set of spot light sources are arranged.

In another embodiment, the angle between the projection of the first light in the plane P and the line 1 is from 37.5° to 52.5°, and the angle between the projection of the second light in the plane P and the line 1 is from 37.5° to 52.5°.

In another embodiment, the distance between the first light source 1a and the second light source 1b is the same as that between the first light source ka and the second light source kb.

According to another aspect of the present invention, it provides a detection system for detecting the defect in a transparent substrate at a detection region, including:

a first illumination system, including:

a first set of spot light sources consisting of a plurality of first spot light sources which emit a respective first light, the respective first lights being substantially parallel to each other and converging to a scan line at the detection region, and the first set of spot light sources and the scan line defining a first light plane;

a second set of spot light sources consisting of a plurality of second spot light sources which emit a respective second light, the respective second lights being substantially parallel to each other and converging to the scan line, the second set of spot light sources and the scan line defining a second light plane;

a second illumination system, including:

a third set of spot light sources consisting of a plurality of third spot light sources which emit a respective third light, the respective third lights being substantially parallel to each other and converging to the scan line, and the third set of spot light sources and the scan line defining a third light plane;

a fourth set of spot light sources consisting of a plurality of fourth spot light sources which emit a respective fourth light, the respective fourth lights being substantially parallel to each other and converging to the scan line, the fourth set of spot light sources and the scan line defining a fourth light plane; and an imaging unit for receiving the first lights, the second lights, the third lights and the fourth lights converged at the scan line and conducting the imaging based on these lights, wherein each point on the scan line in the range of the detection region is illuminated by all the first through fourth lights, and the projections of the first and the third lights and the second and the fourth lights, which are converged at each point on the scan line, in a plane P passing the scan line and perpendicular to the transparent substrate are located at different sides of a line in the plane P, which passes the point and is perpendicular to the scan line, and the first and the second light planes and the third and the fourth light planes are located at different sides of the plane P, the second and the third light planes are in superposition with the first and the fourth light planes respectively or are closer to the plane P than the first and the fourth light planes respectively.

In an embodiment, the angle between the projections of the first and the third lights in the plane P and the line 1 is from 37.5° to 52.5°, and the angle between the projections of the second and the fourth lights in the plane P and the line 1 is from 37.5° to 52.5°

In an embodiment, the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

In an embodiment, the first illumination system includes a first light source receptacle in bar shape, the plurality of first spot light sources and the plurality of second spot light sources being mounted on the first light source receptacle; and the second illumination system includes a second light source receptacle in bar shape, the plurality of third spot light sources and the plurality of fourth spot light sources being mounted on the second light source receptacle.

In this embodiment, the plurality of first spot light sources and the plurality of second spot light sources are mounted on the first light source receptacle. In other words, these spot light sources are in the same plane. Of course, those skilled in the art would easily understand that each set of spot light sources and the plurality of second spot light sources may not be mounted on a light source receptacle, but distributed arbitrarily in different planes as long as each set of lights are substantially parallel to each other and provide lighting in one of both directions along the scan line.

In another embodiment, the first set of spot light sources and the second set of spot light sources are arranged on the first light source receptacle in parallel, and the third set of spot light sources and the fourth set of spot light sources are arranged on the second light source receptacle in parallel.

In another embodiment, the first spot light sources and the second spot light sources are alternately arranged on the first light source receptacle in a line, and the third set of spot light sources and the fourth set of spot light sources are alternately arranged on the second light source receptacle in a line.

In another embodiment, the first spot light sources and the second spot light sources are arranged on the first light source receptacle in a line, and the third set of spot light sources and the fourth set of spot light sources are arranged on the second light source receptacle in a line, wherein the first spot light sources locate in the first half of the first light source receptacle and the second spot light sources locate in the second half of the first light source receptacle; and the third set of spot light sources locate in the first half of the second light source receptacle and the fourth set of spot light sources locate in the second half of the second light source receptacle.

According to another aspect of the present invention, it provides a detection system for detecting the defect in a transparent substrate, including:

transparent substrate conveyoring unit, for converyoring a transparent substrate to be detected to a detection region;

a first illumination system, including:

a first line light source, which emits a first light along the first emission direction;

a second line light source, which emits a second light along the second emission direction, wherein the first light and the second light project and converge to a scan line at the detection region, the first line light source and the scan line define a first light plane, the second line light source and the scan line define a second light plane;

a second illumination system, including:

a third line light source, which emits a third light along the third emission direction;

a fourth line light source, which emits a fourth light along the fourth emission direction, wherein the third light and the fourth light project and converge to the scan line, the third line light source and the scan line define a third light plane, the fourth line light source and the scan line define a fourth light plane; and an imaging unit for receiving the first lights, the second lights, the third lights and the fourth lights converged at the scan line and conducting the imaging based on these lights, wherein each point on the scan line in the range of the detection region is illuminated by all the first through fourth lights, and the projections of the first and the third lights and the second and the fourth lights, which are converged at each point on the scan line, in a plane P passing the scan line and perpendicular to the transparent substrate are located at different sides of a line in the plane P, which passes the point and is perpendicular to the scan line, and the first and the second light planes and the third and the fourth light planes are located at different sides of the plane P, the second and the third light planes are in superposition with the first and the fourth light planes respectively or are closer to the plane P than the first and the fourth light planes respectively.

In an embodiment, the angle between the projections of the first and the third lights in the plane P and the line 1 is from 37.5° to 52.5°, and the angle between the projections of the second and the fourth lights in the plane P and the line 1 is from 37.5° to 52.5°.

In an embodiment, the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

In another embodiment, the first line light source, the second line light source, the third line light source and the fourth line light source include a plurality of spot light sources, respectively.

Other objects and results of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding feature and/or functionality.

DETAILED DESCRIPTION

The embodiment of the present invention will be described hereinafter in more detail with reference to the drawings.

First Embodiment

Figure 3:
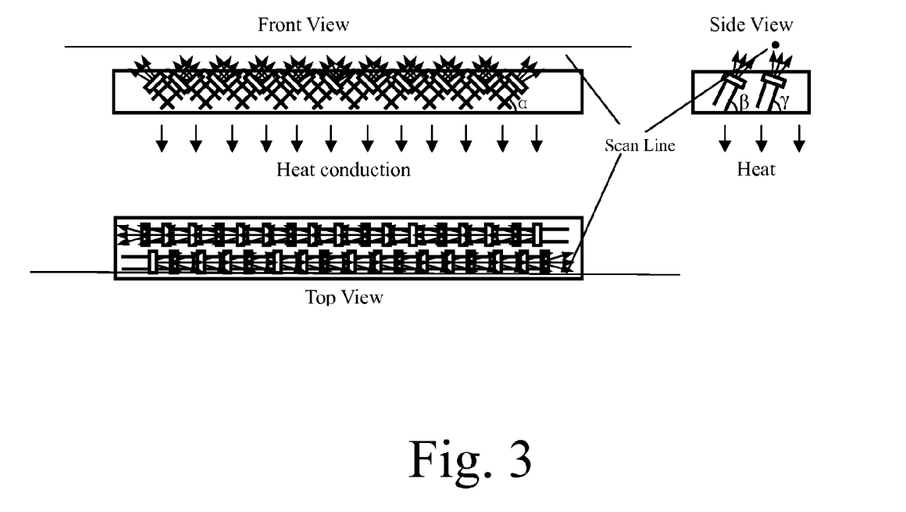
FIG. 3 shows an illumination system for detecting the defect in a transparent substrate in accordance with an embodiment of the present invention.

FIG. 3 shows an illumination system for detecting the defect in a transparent substrate in accordance with the first embodiment of the present invention, wherein the illumination system is composed of two sets of spot light sources, such as LED elements.

As shown in FIG. 3, the two sets of spot light sources are substantially arranged in parallel in a light source receptacle in bar shape along the longitudinal direction of the receptacle. Each LED element in the first set emits a respective first light and the respective first lights are substantially parallel to each other. Likewise, each LED element in the second set emits a respective second light and the respective second lights are substantially parallel to each other.

Referring to FIG. 3, the line or dot above the transparent substrate represents the scan line of line scan CCD camera. CCD camera focuses on the surface parallel to paper in top view and containing scan line. In side view, scan line is perpendicular to the document surface, so it's a dot. The direction of two parallel LED lines is parallel with scan line so that the whole scan line could be illuminated.

As shown in top view and front view of FIG. 3, LED elements in the two sets lean to different directions along LED line. LED elements in the first set lean to the left and LED elements in the second set lean to the right. In other words, the projections of the first and the second lights, which are converged at each point on the scan line, in a plane P (i.e., the paper plane) passing the scan line and perpendicular to the light source receptacle are located at different sides of a line in the plane P, which passes the point and is perpendicular to the scan line. Preferably, the angle α between the projection of the first light in the plane P and the line 1 is from 37.5° to 52.5°, and the angle α between the projection of the second light in the plane P and the line 1 is from 37.5° to 52.5°.

With this structure, every point in scan line can have lighting from both directions along scan line.

Furthermore, lighting perpendicular to scan line in focused surface of CCD camera is also required so that the defects, mostly bubble, with minor axis along with scan line could be well illuminated.

So LED element should also lean to the direction perpendicular to scan line in top view with different angles β and γ as shown in side view of FIG. 3. In other words, the illumination system including the two sets of LED elements should not be positioned right down the scan line. Since two such illumination systems, disposed in different sides of the scan line, are adopted as the illumination source used in the detection system, at least four sets of lights mentioned above could be provided to provide near isotropic illumination.

Therefore, with this design, defect locating in focused surface of CCD camera could be well illuminated whatever axis is parallel to the scan line.

In the present embodiment, the illumination system for detecting the defect in a transparent substrate is composed of two sets (lines) of LED elements. However, it is only for simplicity purpose of example. As is well-known in the art, the number of the lines could be 2, 3 and so on, depending on the specific application and detailed requirements.

In the present embodiment, the first spot light sources, such as the LED elements, are substantially arranged on the receptacle along a straight line and the second spot light sources are substantially arranged on the receptacle along a straight line.

However, although not shown in the figure, it can be readily occur to those skilled in the art that, in the modification of the first embodiment, the receptacle may not be planar, but may be an arc shape when used for detecting the glass in arc shape, for example, the glass used for automobile.

In that case, the first spot light sources are substantially arranged on the arc-shape receptacle along a curve and the second spot light sources are substantially arranged on the receptacle along a curve, as long as these two curves are parallel to each other and fit for the scan line in arc shape.

Second Embodiment

Figure 4:
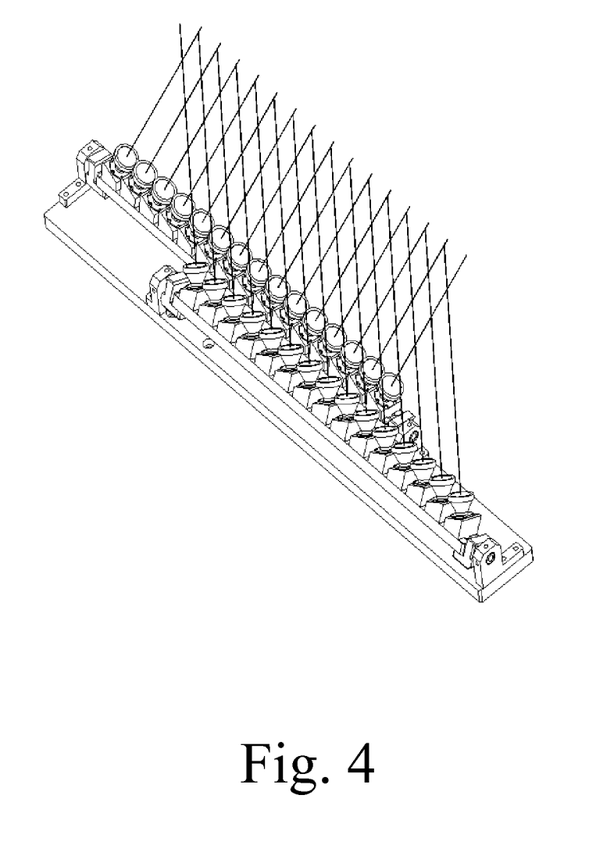
FIG. 4 shows an illumination system for detecting the defect in a transparent substrate in accordance with another embodiment of the present invention.

In accordance with the second embodiment of the present invention, as shown in FIG. 4, the basic idea thereof is the same as that of the first embodiment. The only difference between the second embodiment and the first embodiment is that, in the second embodiment, the two sets of spot light sources are not arranged in parallel, but are arranged in a line.

See FIG. 4, the first set of spot light sources and the second set of spot light sources locate in different half of the receptacle in the longitudinal direction.

Similar to the first embodiment, LED elements in the first set lean to the left and LED elements in the second set lean to the right. In other words, the projections of the first and the second lights, which are converged at each point on the scan line, in a plane P (i.e., the paper plane) passing the scan line and perpendicular to the light source receptacle are located at different sides of a line in the plane P, which passes the point and is perpendicular to the scan line. Preferably, the angle α between the projection of the first light in the plane P and the line 1 is from 37.5° to 52.5°, and the angle α between the projection of the second light in the plane P and the line 1 is from 37.5° to 52.5°.

With this structure, every point in scan line can have lighting from both directions along scan line.

In the present embodiment, the first spot light sources, such as the LED elements, are substantially arranged on the receptacle along a straight line and the second spot light sources are substantially arranged along the same straight line.

However, although not shown in the figure, it can be readily occur to those skilled in the art that, in the modification of the second embodiment, the receptacle may not be planar, but may be an arc shape when used for detecting the glass in arc shape, for example, the glass used for automobile.

In that case, the first spot light sources are substantially arranged on the arc-shape receptacle along a curve and the second spot light sources are substantially arranged along the same curve, as long as the curve fits for the scan line in arc shape.

Third Embodiment

In accordance with the third embodiment of the present invention, although not shown in the figure, the basic idea thereof is the same as that of the first embodiment and the second embodiment. The only difference between the third embodiment and the former two embodiments is that, in the third embodiment, the first spot light sources and the second spot light sources are alternately arranged on the light source receptacle in a line.

In the present embodiment, the first spot light sources, such as the LED elements, are substantially arranged on the receptacle along a straight line and the second spot light sources are substantially arranged along the same straight line.

However, similar to the former two embodiments, it can be readily occur to those skilled in the art that, in the modification of the third embodiment, the receptacle may not be planar, but may be an arc shape when used for detecting the glass in arc shape, for example, the glass used for automobile.

In that case, the first spot light sources and the second spot light sources are substantially alternately arranged on the arc-shape receptacle along a curve, as long as the curve fits for the scan line in arc shape.

Fourth Embodiment

In accordance with the fourth embodiment of the present invention, although not shown in the figure, the basic idea thereof is the same as that of the previous embodiments.

The illumination system of the fourth embodiment includes two sets of spot light sources arranged in a light source receptacle in bar shape.

The first set of spot light sources includes a plurality of first light sources a and they are substantially arranged in a line to be a first line of spot light sources $1a, 2a, \ldots ka, \ldots nb$ along the longitudinal direction of the receptacle. The number n of the spot light sources may be larger than 2, and each first light source a emits a first light.

The second set of spot light sources includes a plurality of second light sources b and they are substantially arranged in a line to be a second line of spot light sources $1b, 2b, \ldots kb, \ldots nb$ along the longitudinal direction of the receptacle. The number n of the spot light sources may be larger than 2, and each second light source b emits a second light.

The first light emitted by the first light source $1a$ and the second light emitted by the corresponding second light source $1b$ converge to a first scan dot $1s, \ldots$, the first light emitted by the first light source ka and the second light emitted by the corresponding second light source kb converge to a kth scan dot ks, ..., the first light emitted by the first light source na and the second light emitted by the corresponding second light source nb converge to an nth scan dot ns, and the first scan dot $1s, \ldots$, the kth scan dot ks, ..., and the nth scan dot ns compose a continuous straight line or cure, which may be the scan line of the detection system including the illumination system.

Where, the projections of the first and the second lights, which are converged at each point on the scan line, in a plane P passing the scan line and perpendicular to the transparent substrate are located at different sides of a line in the plane P, which passes the point and is perpendicular to the scan line.

In the present embodiment, the lines in which the first set of spot light sources and the second set of spot light sources are arranged are substantially parallel to each other. As a modification of the present embodiment, the line in which the first set of spot light sources are arranged is in the extended line of the line in which the second set of spot light sources are arranged.

Preferably, in an embodiment of the present invention, the angle between the projection of the first light in the plane P and the line 1 is from 37.5° to 52.5°, and the angle between the projection of the second light in the plane P and the line 1 is from 37.5° to 52.5°.

In the present embodiment, the distance between the first light source $1a$ and the second light source $1b$ is the same as that between the first light source ka and the second light source kb. In a preferred embodiment, the distances between the corresponding first light source and the second light source are the same.

Fifth Embodiment

Figure 5:
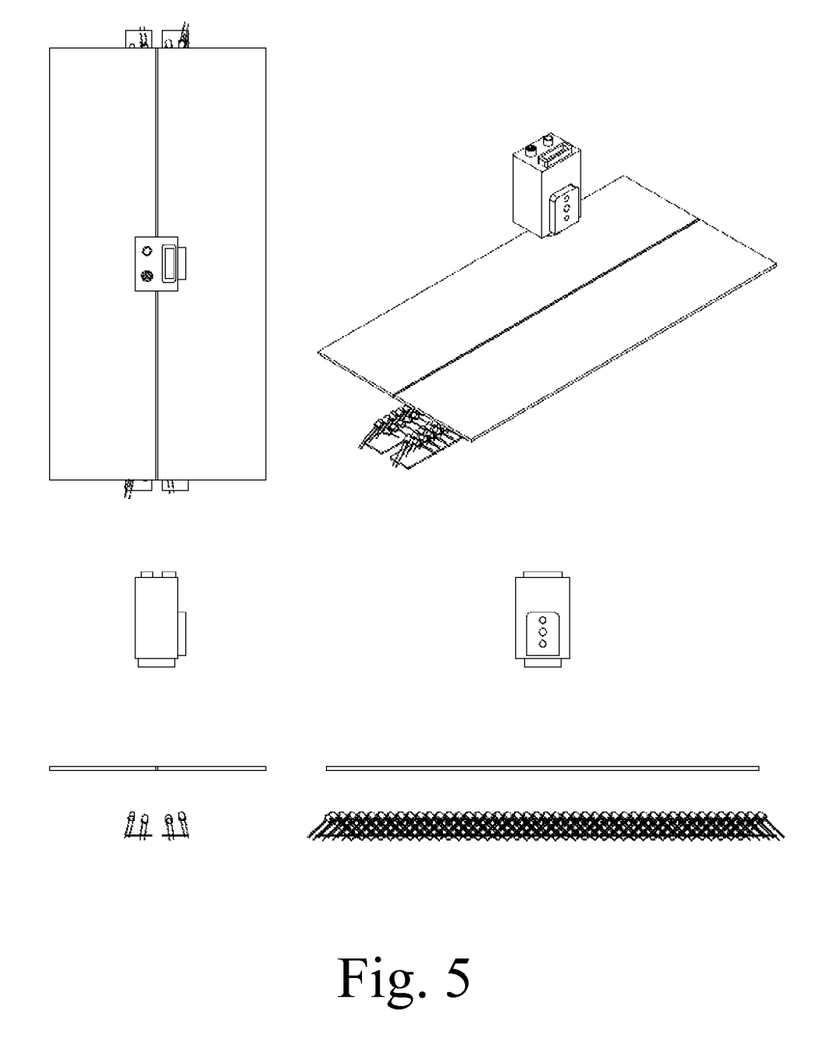
FIG. 5 shows a detection system for detecting the defect in a transparent substrate at a detection region in accordance with an embodiment of the present invention.

FIG. 5 shows a detection system for detecting the defect in a transparent substrate at a detection region in accordance with the fifth embodiment of the present invention.

As shown in FIG. 5, the detection system includes two illumination systems in accordance with the first embodiment and an imaging unit, which may be a CCD camera. As shown, the two illumination systems are arranged in different sides of the scan line of the CCD camera.

The first illumination system on the left side of the scan line includes two sets of spot light sources.

The first set of spot light sources consists of a plurality of first spot light sources which emit a respective first light, the respective first lights are substantially parallel to each other and converge to the scan line, and the first set of spot light sources and the scan line define a first light plane.

The second set of spot light sources consists of a plurality of second spot light sources which emit a respective second light, the respective second lights are substantially parallel to each other and converge to the scan line, the second set of spot light sources and the scan line define a second light plane.

In the present embodiment, the angle between the first light plane and the second light plane is from 0° to 15°.

Similarly, the second illumination system on the right side of the scan line includes two sets of spot light sources as well.

The third set of spot light sources consists of a plurality of third spot light sources which emit a respective third light, the respective third lights are substantially parallel to each other and converge to the scan line, and the third set of spot light sources and the scan line define a third light plane.

The fourth set of spot light sources consists of a plurality of fourth spot light sources which emit a respective fourth light, the respective fourth lights are substantially parallel to each other and converge to the scan line, the fourth set of spot light sources and the scan line define a fourth light plane.

In the present embodiment, the angle between the third light plane and the fourth light plane is from 0°-15°.

The maximum angle between the first and the fourth light planes and the plane P is 52.5°, and the minimum angle between the second and the third light planes and the plane P is 37.5°. Please note that, each point on the scan line in the range of the detection region is illuminated by all the first through fourth lights.

As shown in FIG. 5, the imaging unit receives the first lights, the second lights, the third lights and the fourth lights converged at the scan line and conducts the imaging based on these lights to detect the defect in the transparent substrate.

Further, it should be noted that, FIG. 5 is illustrated as an example of the detection system in accordance with the present invention. It would be easily understood by those skilled in the art that, the detection system may include illumination systems other than the illumination system of the first embodiment.

For example, the detection system may include illumination systems in accordance with the second through the fourth embodiments. Alternatively, the two illumination systems arranged in different sides of the scan line of the CCD camera may be different. For example, the first illumination system on the left side of the scan line may be the illumination system in accordance with the first embodiment of the present invention, and the second illumination system on the right side of the scan line may be the illumination system in accordance with the second embodiment of the present invention.

Furthermore, the four sets of spot light sources may not be mounted in the receptacle as that in the above-mentioned first through fourth embodiments. For example, the spot light sources in each set may not in the same plane, i.e., the spot light sources in each set may be distributed arbitrarily, as long as the respective lights emitted by each spot light source in one set are substantially parallel to each other and converge to the scan line.

Those skilled in the art would conceive many kinds of combinations of the two illumination systems used in the detection system.

Sixth Embodiment

The detection system in accordance with the sixth embodiment of the present invention is similar to that of the fifth embodiment.

The detection system includes a transparent substrate conveyoring unit for converyoring a transparent substrate to be detected to a detection region and two illumination systems.

The first illumination system includes a first line light source, which emits a first light along the first emission direction, and a second line light source, which emits a second light along the second emission direction. The first light and the second light project and converge to a scan line at the detection region, the first line light source and the scan line define a first light plane, the second line light source and the scan line define a second light plane.

The second illumination system, includes a third line light source, which emits a third light along the third emission direction, and a fourth line light source, which emits a fourth light along the fourth emission direction, wherein the third light and the fourth light project and converge to the scan line, the third line light source and the scan line define a third light plane, the fourth line light source and the scan line define a fourth light plane.

Similarly, each point on the scan line in the range of the detection region is illuminated by all the first through fourth lights. Further, the projections of the first and the third lights and the second and the fourth lights, which are converged at each point on the scan line, in a plane P passing the scan line and perpendicular to the transparent substrate are located at different sides of a line in the plane P, which passes the point and is perpendicular to the scan line. The first and the second light planes and the third and the fourth light planes are located at different sides of the plane P, the second and the third light planes are in superposition with the first and the fourth light planes respectively or are closer to the plane P than the first and the fourth light planes respectively.

The detection system further includes an imaging unit for receiving the first lights, the second lights, the third lights and the fourth lights converged at the scan line and conducting the imaging based on these lights.

As can be seen from the above, the difference between the detection system of the sixth embodiment and that of the fifth embodiment is that the light source used in the present embodiment is line light source, but not spot light source.

Of course, in the modification of the present embodiment, the first line light source, the second line light source, the third line light source and the fourth line light source may include a plurality of spot light sources, respectively.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "including" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A detection system for detecting the defect in a transparent substrate at a detection region, comprising:
  a first illumination system, comprising:
    a first set of spot light sources consisting of a plurality of first spot light sources which emit a respective first light, the respective first lights being substantially parallel to each other and converging to a scan line at the detection region, and the first set of spot light sources and the scan line defining a first light plane;
    a second set of spot light sources consisting of a plurality of second spot light sources which emit a respective second light, the respective second lights being substantially parallel to each other and converging to the scan line, the second set of spot light sources and the scan line defining a second light plane;
  a second illumination system, comprising:
    a third set of spot light sources consisting of a plurality of third spot light sources which emit a respective third light, the respective third lights being substantially parallel to each other and converging to the scan line, and the third set of spot light sources and the scan line defining a third light plane;
    a fourth set of spot light sources consisting of a plurality of fourth spot light sources which emit a respective fourth light, the respective fourth lights being substantially parallel to each other and converging to the scan line, the fourth set of spot light sources and the scan line defining a fourth light plane; and
  an imaging unit for receiving the first lights, the second lights, the third lights and the fourth lights converged at the scan line and conducting the imaging based on these lights,
  wherein each point on the scan line in the range of the detection region is illuminated by all the first through fourth lights, and
  the projections of the first and the third lights and the second and the fourth lights, which are converged at each point on the scan line, in a plane P passing the scan line and perpendicular to the transparent substrate are located at different sides of a line 1 in the plane P, which passes the point and is perpendicular to the scan line, and
  the first and the second light planes and the third and the fourth light planes are located at different sides of the plane P, the second and the third light planes are in superposition with the first and the fourth light planes respectively or are closer to the plane P than the first and the fourth light planes respectively.

2. The detection system according to claim 1, wherein the angle between the projections of the first and the third lights in the plane P and the line 1 is from 37.5° to 52.5°, and the angle between the projections of the second and the fourth lights in the plane P and the line 1 is from 37.5° to 52.5°.

3. The detection system according to claim 1, wherein the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

4. The detection system according to claim 1, wherein
the first illumination system comprises a first light source receptacle in bar shape, the plurality of first spot light sources and the plurality of second spot light sources being mounted on the first light source receptacle; and
the second illumination system comprises a second light source receptacle in bar shape, the plurality of third spot light sources and the plurality of fourth spot light sources being mounted on the second light source receptacle.

5. The detection system according to claim 4, wherein
the first set of spot light sources and the second set of spot light sources are arranged on the first light source receptacle in parallel, and the third set of spot light sources and the fourth set of spot light sources are arranged on the second light source receptacle in parallel.

6. The detection system according to claim 4, wherein
the first spot light sources and the second spot light sources are alternately arranged on the first light source receptacle in a line, and the third set of spot light sources and the fourth set of spot light sources are alternately arranged on the second light source receptacle in a line.

7. The detection system according to claim 4, wherein
the first spot light sources and the second spot light sources are arranged on the first light source receptacle in a line, and the third set of spot light sources and the fourth set of spot light sources are arranged on the second light source receptacle in a line, wherein
the first spot light sources locate in the first half of the first light source receptacle and the second spot light sources locate in the second half of the first light source receptacle; and
the third set of spot light sources locate in the first half of the second light source receptacle and the fourth set of spot light sources locate in the second half of the second light source receptacle.

8. An illumination system for detecting the defect in a transparent substrate, comprising
light source receptacle in bar shape;
a plurality of first spot light sources, each emitting a respective first light, the respective first lights being substantially parallel to each other and the first spot light sources being arranged to a first line of spot light sources along the longitudinal direction of the receptacle; and
a plurality of second spot light sources, each emitting a respective second light, the respective second lights being substantially parallel to each other and the second spot light sources being arranged to a second line of spot light sources along the longitudinal direction of the receptacle, wherein
the first line of spot light sources and the second line of spot light sources are substantially arranged in a line, the first line of spot light sources and the second line of spot light sources locate in difference half of the receptacle in the longitudinal direction, the first light and the second light converge to a scan line, and the projections of the first and the second lights, which are converged at each point on the scan line, in a plane P passing the scan line and perpendicular to the transparent substrate are located at different sides of a line in the plane P, which passes the point and is perpendicular to the scan line.

9. The illumination system according to claim 8, wherein the angle between the projection of the first light in the plane P and the line 1 is from 37.5° to 52.5°, and the angle between the projection of the second light in the plane P and the line 1 is from 37.5° to 52.5°.

10. The illumination system according to claim 8, wherein the first spot light sources are substantially arranged on the receptacle along a straight line and the second spot light sources are substantially arranged on the receptacle along the straight line.

11. The illumination system according to claim 8, wherein the first spot light sources are substantially arranged on the receptacle along a curve and the second spot light sources are substantially arranged on the receptacle along the curve.

12. An illumination system for detecting the defect in a transparent substrate, comprising
light source receptacle in bar shape;
a plurality of first spot light sources, each emitting a respective first light, the respective first lights being substantially parallel to each other and the first spot light sources being arranged to a first line of spot light sources along the longitudinal direction of the receptacle; and
a plurality of second spot light sources, each emitting a respective second light, the respective second lights being substantially parallel to each other and the second spot light sources being arranged to a second line of spot light sources along the longitudinal direction of the receptacle, wherein
the first line of spot light sources and the second line of spot light sources are substantially arranged in parallel, the first light and the second light converge to a scan line, and the projections of the first and the second lights, which are converged at each point on the scan line, in a plane P passing the scan line and perpendicular to the transparent substrate are located at different sides of a line in the plane P, which passes the point and is perpendicular to the scan line.

13. The illumination system according to claim 12, wherein the angle between the projection of the first light in the plane P and the line 1 is from 37.5° to 52.5°, and the angle between the projection of the second light in the plane P and the line 1 is from 37.5° to 52.5°.

14. The illumination system according to claim 12, wherein the first spot light sources are substantially arranged on the receptacle along a straight line and the second spot light sources are substantially arranged on the receptacle along a straight line.

15. The illumination system according to claim 12, wherein the first spot light sources are substantially arranged on the receptacle along a curve and the second spot light sources are substantially arranged on the receptacle along a curve.

16. A detection system for detecting the defect in a transparent substrate, comprising:
transparent substrate conveyoring unit, for converyoring a transparent substrate to be detected to a detection region;
a first illumination system, comprising:
a first line light source, which emits a first light along the first emission direction;
a second line light source, which emits a second light along the second emission direction, wherein
the first light and the second light project and converge to a scan line at the detection region, the first line light source and the scan line define a first light plane, the second line light source and the scan line define a second light plane;

a second illumination system, comprising:
a third line light source, which emits a third light along the third emission direction;
a fourth line light source, which emits a fourth light along the fourth emission direction, wherein
the third light and the fourth light project and converge to the scan line, the third line light source and the scan line define a third light plane, the fourth line light source and the scan line define a fourth light plane; and
an imaging unit for receiving the first lights, the second lights, the third lights and the fourth lights converged at the scan line and conducting the imaging based on these lights,
wherein each point on the scan line in the range of the detection region is illuminated by all the first through fourth lights, and
the projections of the first and the third lights and the second and the fourth lights, which are converged at each point on the scan line, in a plane P passing the scan line and perpendicular to the transparent substrate are located at different sides of a line in the plane P, which passes the point and is perpendicular to the scan line, and
the first and the second light planes and the third and the fourth light planes are located at different sides of the plane P, the second and the third light planes are in superposition with the first and the fourth light planes respectively or are closer to the plane P than the first and the fourth light planes respectively.

17. The detection system according to claim 16, wherein the angle between the projections of the first and the third lights in the plane P and the line 1 is from 37.5° to 52.5°, and the angle between the projections of the second and the fourth lights in the plane P and the line 1 is from 37.5° to 52.5°.

18. The detection system according to claim 16, wherein the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

19. The detection system according to claim 16, wherein the first line light source, the second line light source, the third line light source and the fourth line light source comprise a plurality of spot light sources, respectively.

20. An illumination system for detecting the defect in a transparent substrate, comprising
light source receptacle in bar shape;
a first set of spot light sources, comprising a plurality of first light sources a, the first light sources a being substantially arranged in a line to a first line of spot light sources ($1a, 2a, \ldots ka, \ldots na$) along the longitudinal direction of the receptacle, wherein n is an integer larger than 2, k is an integer between 1 and n, and each first light source a emits a first light; and
a second set of spot light sources, comprising a plurality of second light sources b, the second light sources b being substantially arranged in a line to a second line of spot light sources ($1b, 2b, \ldots kb, \ldots, nb$) along the longitudinal direction of the receptacle, wherein each second light source b emits a second light, wherein
the first light emitted by the first light source 1a and the second light emitted by the corresponding second light source $1b$ converge to a first scan dot $1s, \ldots$, the first light emitted by the first light source ka and the second light emitted by the corresponding second light source kb converge to a kth scan dot ks, $\ldots$, the first light emitted by the first light source na and the second light emitted by the corresponding second light source nb converge to an nth scan dot ns, and the first scan dot $1s, \ldots$, the kth scan dot ks, $\ldots$, and the nth scan dot ns are substantially arranged in a continuous straight line or curve,
wherein the projections of the first and the second lights, which are converged at each point on the scan line, in a plane P passing the scan line and perpendicular to the transparent substrate are located at different sides of a line in the plane P, which passes the point and is perpendicular to the scan line.

21. The illumination system according to claim 20, wherein
the lines in which the first set of spot light sources and the second set of spot light sources are arranged are substantially parallel to each other.

22. The illumination system according to claim 20, wherein
the line in which the first set of spot light sources are arranged is in the extended line of the line in which the second set of spot light sources are arranged.

23. The illumination system according to claim 20, wherein
the angle between the projection of the first light in the plane P and the line 1 is from 37.5° to 52.5°, and the angle between the projection of the second light in the plane P and the line 1 is from 37.5° to 52.5°.

24. The illumination system according to claim 20, wherein
the distance between the first light source $1a$ and the second light source $1b$ is the same as that between the first light source ka and the second light source kb.

25. The detection system according to claim 2, wherein the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

26. The detection system according to claim 17, wherein the maximum angle between the first and the fourth light planes and the plane P is 52.5°, the angle between the first light plane and the second light plane is from 0° to 15°, the angle between the third light plane and the fourth light plane is from 0° to 15°, and the minimum angle between the second and the third light planes and the plane P is 37.5°.

* * * * *